United States Patent
Hansson (12)

(10) Patent No.: US 6,312,417 B1
(45) Date of Patent: Nov. 6, 2001

(54) INDIVIDUAL WRAPPING FOR ABSORBENT PRODUCTS WITH ATTACHMENT FLAPS

(75) Inventor: Roy Hansson, Mölndal (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/051,412

(22) PCT Filed: Oct. 23, 1996

(86) PCT No.: PCT/SE96/01359

§ 371 Date: Apr. 7, 1998

§ 102(e) Date: Apr. 7, 1998

(87) PCT Pub. No.: WO97/16143

PCT Pub. Date: May 9, 1997

(30) Foreign Application Priority Data

Oct. 30, 1995 (SE) .................................................. 9503818

(51) Int. Cl.[7] .............................. A61F 13/15; A61F 13/20
(52) U.S. Cl. ................................ 604/385.02; 604/385.04; 604/385.05; 604/385.01; 604/385.03
(58) Field of Search ............................... 604/358, 385.02, 604/385.04, 385.05, 385.01, 385.03, 386, 387, 389, 390; 206/438, 439, 440, 813; 602/54, 56, 57, 58; D9/416; D3/203

(56) References Cited

U.S. PATENT DOCUMENTS

| 4,285,343 | 8/1981 | McNair | 128/287 |
|---|---|---|---|
| 4,556,146 | 12/1985 | Swanson et al. | 206/440 |
| 4,608,047 | 8/1986 | Mattingly | 604/387 |
| 4,917,697 | * 4/1990 | Osborn, III et al. | 604/387 |
| 5,181,610 | 1/1993 | Quick et al. | 206/447 |
| 5,295,988 | * 3/1994 | Muckenfuhs et al. | 604/385.2 |
| 5,683,377 | * 11/1997 | Mizutani | 604/390 |
| 6,074,376 | 6/2000 | Mills . | |

FOREIGN PATENT DOCUMENTS 0 130 848 A2   1/1985   (EP) .

(List continued on next page.)

*Primary Examiner*—John G. Weiss
*Assistant Examiner*—Michele Kidwell
(74) *Attorney, Agent, or Firm*—Burns, Doane, Swecker & Mathis, L.L.P.

(57) ABSTRACT

The invention concerns an absorbent product such as a sanitary napkin, a pantyliner or an incontinence protector with an essentially elongated shape which has at least one attachment flap (22) arranged on a longitudinal side edge (8) of the product and folded over the liquid-permeable surface (2) of the product and having at least one adhesive attachment means (24) on the surface of the attachment flap (22) facing away from the product in the folded condition, and further a packaging wrapper (17) also of essentially longitudinal shape, whereby the packaging wrapper (17) lies on the liquid-impermeable surface (3) of the product and is folded together with the product along at least one transverse fold line (14) on the product to form a package (30). A distinguishing feature of the invention is that a protective layer (26) is arranged with a release agent-treated surface on the protective flap (26) removably lying over the adhesive attachment means (24) on the attachment flap (22), and has a part (28) which is firmly attached to the packaging wrapper (17) near a transverse end edge (19) on the packaging wrapper (17), wherein the joint (29) between the protective layer (26) and the packaging wrapper (17) is stronger than the connection between the protective flap (26) and the adhesive fastening means on the attachment flap (22), and remains in place even after the package (30) is opened.

13 Claims, 4 Drawing Sheets

FOREIGN PATENT DOCUMENTS

| | | |
|---|---|---|
| 0 134 086 B1 | 3/1985 | (EP) . |
| 0 357 000 A1 | 3/1990 | (EP) . |
| 0750896 | 1/1997 | (EP) . |
| 2 221 667 A | 2/1990 | (GB) . |
| 2 277 914 A | 11/1994 | (GB) . |
| 455 668 | 8/1988 | (SE) . |
| 459 067 | 6/1989 | (SE) . |
| WO 91/18574 | 12/1991 | (WO) . |
| WO 93/09743 | 5/1993 | (WO) . |
| WO 94/04111 | 3/1994 | (WO) . |
| WO 94/14398 | 7/1994 | (WO) . |
| WO97/15261 | 5/1997 | (WO) . |
| 884054 | 6/1998 | (ZA) . |

* cited by examiner

INDIVIDUAL WRAPPING FOR ABSORBENT PRODUCTS WITH ATTACHMENT FLAPS

The present invention concerns an absorbent product such as a sanitary napkin, pantyliner or an incontinent protector, which is packaged in a protective wrapper and is equipped with at least one attachment flap. The attachment flap is arranged on a longitudinal side edge of the product and comprises an adhesive attachment means.

There are many reasons why it is advantageous to pack single absorbent products of the type described in the introduction in individual protective wrappers. In this manner small handy packages can be obtained which can easily and comfortably be taken along in a handbag or a pocket, and out of which an article can quickly and easily be produced when necessary. Such so-called individual wrappers ensure that the article is protected against soiling and damage before use and is therefore much appreciated by the users. By suitably shaping the package wrapper it can also be used as a wrapper for used articles, which can thus be thrown away in a hygienic and aesthetically acceptable manner.

The usual way to fasten an absorbent product such as a sanitary napkin or the like inside a pair of underpants during use is to arrange a fastening surface in the form of pressure-sensitive, self-adhesive glue on the side of the napkin which during use is intended to be in contact with the underpants of the user. In order to prevent self-adhesion problems with the adhesive surface during storage and transportation of the napkin, the attachment adhesive is usually protected with a special, removable material tape made of release agent treated paper or the like. When the product is to be used, the protective tape is removed so that the adhesive is exposed and can be used for attaching the product in the underpants of the user. The protective tape has afterwards no further function but is thrown away once it has been removed from the attachment adhesive. The use of such protective tapes has a number of disadvantages. For example, it is difficult to handle the protective tapes at the same time as the product is being used, especially if the product is equipped with several different protective tapes which have to be removed. The use of protective tapes also means that an excessive amount of material is consumed, which is a disadvantage from both the environmental and the energy points of view as well as the cost point of view.

It has therefore become more common to provide absorbent products of this sort with a removable protective wrapping which fulfills the double function of protecting the fastening adhesive against undesirable adhesion until the use of the product, as well as forming an individual wrapper for the product. In U.S. Pat. No. 4,556,146, ZA 884,054, SE 459,067, GB 2,221,667, EP 357,000, U.S. Pat. No. 5,181,610, WO 91/18574, WO 93/09743 and WO 94/04111, absorbent products equipped with protective wrappers are described, which form both the wrapper for the product and a protector for the attachment adhesive.

A big disadvantage of these earlier prior art protective wrappers is, however, that they only partly solve the problem of eliminating the use of separate protective tapes for the attachment adhesive on so-called wing napkins. In order to reduce the risk of side edge leakage and in order to improve the fastening security and reduce the deformation of the absorbent product during use, a considerable share of, above all, sanitary napkins which are sold are equipped with flexible fastening flaps, also known as wings, on the side edges of the product. Such fastening flaps are intended during use to be bent around the leg edges of the underpants of the user and fastened against the outside of the underpants by means of surfaces of pressure-sensitive self-adhesive glue on the attachment flaps. Examples of sanitary napkins with attachment flaps are shown in SE 455,668, U.S. Pat. No. 4,285,343, EP 130,848, EP 134,086 and U.S. Pat. No. 4,608,047.

In the known removable wrappings the attachment adhesive on the attachment flaps on a wing napkin must be protected by a special protective tape. Before the product can be used, the user must remove and throw away this protective tape. Naturally, the advantage of using the wrapping material as a protector for the attachment adhesive of the product is greatly diminished. Furthermore, the known wing release tapes are small and difficult for the user to handle. A special problem thereof is that they easily become statically charged and fasten onto the user's skin and clothes. Much effort has therefore been made to solve the problem of eliminating the special protective tapes for the attachment adhesive on the wings.

EP 532,649 describes an individually wrapped sanitary napkin with a removable protective wrapper, which can also be used to package a sanitary napkin with attachment flaps. The protective wrapper extends laterally beyond the attachment flaps when these flaps are in a position where they protrude straight out from the side edges of the sanitary napkin. Such an arrangement makes it possible to avoid the use of special protective tapes for the fastening flaps. However, it means, on the other hand, that approximately twice as much packaging material as used in conventional individual wrappers is required. This is naturally a serious disadvantage as the large consumption of material makes the sanitary napkin more expensive and is negative from an environmental point of view. Furthermore, the extra wrapping material must be handled and folded out by the user, which makes it complicated and cumbersome to take the wing napkin out of the wrapping.

WO 94/14398 describes a wing napkin with a pattern of attachment adhesive, which in combination with a special folding of the fastening flaps allows the use of a single protective layer in order to cover all of the adhesive surfaces on both the napkin itself and the attachment flaps. The disadvantage of this known napkin is, however, that it is limited to a certain combination of attachment flap shapes and adhesive surface appearance and positioning. For example, it is not possible to arrange the attachment adhesive along the longitudinal side edges of the sanitary napkin, which is normally desirable. Furthermore, WO 94/14398 does not give any suggestion to how to make an individual wrapper for a sanitary napkin.

Similar problems occur in the packaging described in GB 2,227,914, where a protective layer for adhesive surfaces on an absorbent article is fixed at an edge inside a small bag-like wrapper. When the article is taken out of the bag, the protective layer is folded away from the wrapper and in this way comes loose from the adhesive surface. Such a wrapper, however, limits the possibilities of where the attachment adhesive can be placed on the article and how the article can be folded together before it is packaged. It is furthermore almost impossible to use the empty wrapper in order to throw away a used article because a used article is soiled, bulky and deformed and difficult to fold together in a hygienic manner to the same compact format as an unused article.

With the present invention, however, an individually packaged absorbent product of the type mentioned in the introduction has been achieved, in which the problem of earlier known such products is avoided.

The product according to the invention is distinguished primarily by a protective layer being arranged with a release-agent-treated surface on the protective flap removably covering the adhesive fastening means on the attachment flap and having a part which is firmly joined to the packaging wrapper near a transverse end edge on the packaging wrapper, wherein the connection between the protective layer and the packaging wrapper is stronger than the connection between the protective flap and the adhesive fastening means on the attachment flap and remains in place even after the packaging has been opened.

In accordance with the invention, a number of advantages are achieved by equipping the packaging wrapper with a special protective flap, fixed to the wrapper, for the attachment adhesive on the wings of the product. In this manner, it is actually possible to achieve with a minimum use of material an easily handled individual packaging for absorbent products equipped with attachment flaps. The invention completely eliminates the manipulation of special protective tapes for the attachment adhesive on the attachment flaps when the article is taken out of the packaging. In a preferred embodiment, this is achieved by the protective surface automatically coming away from the adhesive surfaces on the fastening flaps in connection with the seams of the packaging being opened. In the opened wrapper the absorbent product lies outstretched with its liquid-impermeable surface against the packaging wrapper, with the fastening flaps folded over the liquid-permeable surface of the product, and with the adhesive surfaces on the attachment flaps exposed for attachment.

The product can subsequently be easily removed from the packaging wrapper and placed in the crotch part of a pair of underpants. The fastening flaps are then folded out from the liquid-permeable surface of the product, brought around the leg edges of the underpants and fastened against the outside of the crotch part of the underpants.

The invention will now be described in more detail with reference to the embodiments which are shown in the appended drawings.

Figure 1:
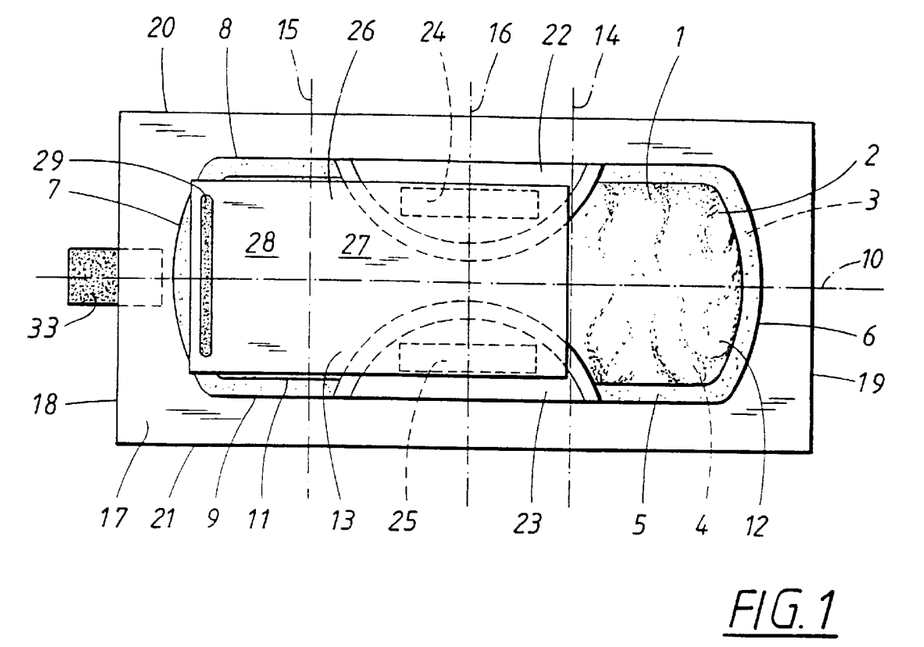
FIG. 1 of the drawings shows a sanitary napkin with attachment flaps placed on a packaging wrapper.

The sanitary napkin 1 shown in FIG. 1 is conventionally constructed and comprises a first liquid-permeable covering layer 2 arranged on the side of the sanitary napkin 1 which during use is intended to be facing towards the user, a second, liquid-impermeable covering layer 3 arranged on the side of the sanitary napkin which during use is intended to be facing away from the user, and an absorption body 4 enclosed between the two covering layers 2,3.

The two covering layers 2,3 extend out past the edges of the absorption body 4, and the protruding parts 5 of the covering layers are mutually joined around the periphery of the absorption body 4, for example by gluing, sewing or through welding with heat or ultrasound.

The material in the liquid-permeable covering layer 2 can be of any suitable type. Examples of common liquid-permeable covering materials are different sorts of bound, nonwoven fibercloths, so-called non-woven materials, perforated plastic films, nets and open-cell or perforated foam material. Different types of laminates, e.g. laminates of non-woven material and plastic film can also be used. However, it is not necessary for the invention that the liquid-permeable layer 2 is a separate material layer but this layer can instead be an integrated part of the absorption body 4.

The liquid-impermeable layer 3 is preferably made from a thin plastic film, or from a nonwoven material which is made liquid-impermeable through coating or treatment with a liquid-resistant material. Naturally, other types of liquid-barrier material can also be used, such as for example plastic foam with closed cells, different liquid-barrier laminates etc. In order that the sanitary napkin 1 should feel airy and comfortable to wear, it is appropriate that the liquid-impermeable layer 3 has a certain permeability for air and water vapour. The liquid-impermeable layer 3 can also be an integrated part of the absorption body 4 and can for example be a skin-like surface on an absorbent foam body.

The sanitary napkin 1 has an elongated nearly rectangular shape and is bounded by two transverse end edges 6,7 and two longitudinal side edges 8 and 9 between these. The sanitary napkin 1 can further be divided along its longitudinal centreline 10 into a first and a second end part 11,12 and a centre part 13 lying between the end parts 11,12. The different parts 11–13 have no definite boundaries between each other but can generally be considered as each taking up approximately one third of the length of the sanitary napkin. The centre part 13, also known as the crotch part, is usually considered to comprise the portion of the absorbent product in which the so-called wetting region is to be found. The wetting region on an absorbent product is the portion of the product which is intended to first receive the emitted body fluids. The size of the end parts 11,12 can vary somewhat but usually the end part which during use faces backwards on the user is considered to be somewhat longer than the end part facing forwards. As the end parts 11,12 on the sanitary napkin 1 shown in FIG. 1 are completely symmetrical, the sanitary napkin can be worn during use with either of the end parts 11,12 facing forwards. The sizes and the positions for the different parts 11–13 of the sanitary napkin along the longitudinal centreline 10 can therefore only be determined when the article is in use.

Two transverse fold lines 14,15 have been drawn in in the Figures, one on each side of the transverse centreline 16 of the sanitary napkin 1. In order to simplify the description of the invention, it has been assumed in the following that the end parts 11,12 and the centre part 13 of the sanitary napkin essentially correspond with the division along the longitudinal centreline 10 of the sanitary napkin, as defined by the fold lines 14,15.

Arranged on the outside of the liquid-impermeable cover layer 3 there is an attachment means (not shown) in the form of at least one surface of self-adhesive pressure-sensitive glue. The attachment means is removably fastened against one surface of a rectangular packaging wrapper 17. The adhesive pattern can usually be one or more longitudinal lines of adhesive, or two or more transverse lines of adhesive. Other patterns can, however, also be used as well as a complete coating of the liquid-impermeable covering layer 3 with adhesive.

The packaging wrapper 17 has, like the sanitary napkin, two transverse end edges 18,19 as well as two longitudinal side edges 20,21 and has a larger length than the sanitary napkin 1, so that it extends out around the edges 6–9 of the sanitary napkin 1 around the whole of its periphery. The packaging wrapper 17 is a sheet of, for example, paper, plastic or another flexible material which is treated with release agents on the surface facing towards the sanitary napkin 1 in order to achieve the desired removable attachment to the attachment means of the sanitary napkin 1. Such a release agent treatment usually consists of a silicon coating. The release agent treatment can be applied over the whole of the surface of the packaging wrapper 17 facing towards the sanitary napkin 1, or can be selectively arranged only on the regions which lie in contact with the fastening means of the sanitary napkin.

Near the centre part 13 of the sanitary napkin 1, the fastening flaps 22,23 are arranged along each of the side edges 8,9. The attachment flaps 22,23 are formed from the parts of the two covering layers 2,3, which extend out past the side edges 8,9 on the absorption body 4 and are laminated together, for example by means of gluing or welding. The attachment flaps 22,23 have further an outwardly rounded shape and are arranged essentially symmetrically about the transverse centreline 16 of the sanitary napkin 1. During use of the sanitary napkin 1 the attachment flaps 22,23 are intended to be folded around the leg edges of the underpants of the user and to be fastened against the underside of the crotchpart of the underpants by means of a region 24,25 of self-adhesive pressure-sensitive glue arranged on the liquid-impermeable covering layer 3 on each of the fastening flaps 22,23.

The two attachment flaps 22,23 are folded in over the liquid-permeable covering layer 2 of the sanitary napkin along the side edges 8,9 of the sanitary napkin. The adhesive 24,25 on the attachment flaps 22,23 is covered by a protective layer 26 of a material which has been treated with a release agent on the surfaces facing towards the flaps 22,23. The protective layer 26 is rectangular and has such a breadth that it can cover the adhesive surfaces 24,25 on both the fastening flaps 22,23. In the longitudinal direction the protective layer 26 has two parts 27,28 of which the first part 27 lies on the adhesive 24,25 on the attachment flaps 22,23 near the centre part 13 of the sanitary napkin 1, while the second part 28 of the protective layer 26 extends away from the attachment flaps 22,23 in over the first end part 11 of the sanitary napkin 1. A transverse thread of adhesive 29 is arranged on the second part 28 of the surface of the protective layer 26 which faces away from the sanitary napkin 1.

Figure 2:
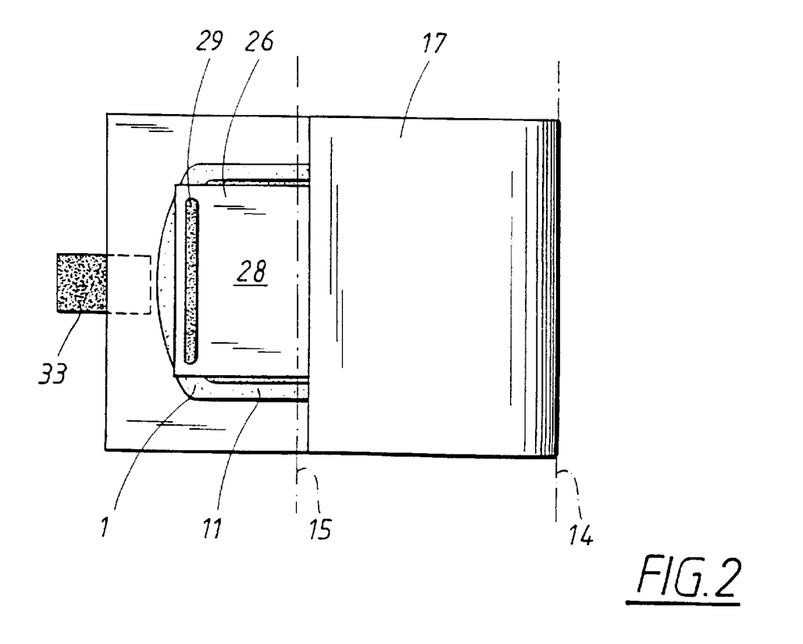
FIG. 2 shows a sanitary napkin and packaging wrapper as in FIG. 1 after being folded a first time.

FIG. 2 shows the configuration of the sanitary napkin 1 and the packaging wrapper 17 after being folded together a first time. The second end part 12 on the napkin 1, over which the protective layer 26 of the fastening flaps 22,23 does not extend, has been folded together with the packaging wrapper 17 over the centre part 13 of the napkin 1 along the first transverse fold line 14. The folding has occurred in a direction towards the liquid-permeable covering layer 2 of the sanitary napkin 1, so that the liquid-permeable covering layer 2 on the second end part 12 of the sanitary napkin is in contact with the liquid-permeable covering layer 2 at the centre part 13 of the sanitary napkin and the packaging wrapper 17 is facing out.

Figure 3:
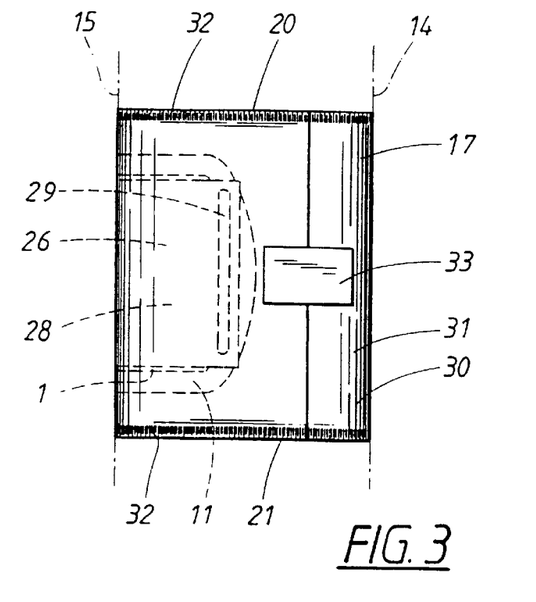
FIG. 3 shows a sanitary napkin and packaging wrapper as shown in FIGS. 1 and 2 after being folded together a second, final time.

The sanitary napkin 1 and the packaging wrapper 17 are folded together once again along the second transverse folding line in FIG. 3. The first end part 11 of the napkin 1 is in this way folded together with the packaging wrapper 17 over the first folded second end part 12 to a handy-sized package. During the second folding the second part 28 of the protective layer 26 of the attachment flaps 22,23 is also folded together with the napkin 1 and the packaging wrapper 17. In this way the transverse bead of adhesive 29 on the second part 28 of the protective layer 26 will in the completely folded individual package 30 be fastened against the outside 31 of the first folded-in part of the packaging wrapper 17.

As can be observed in FIGS. 1–3, the fold lines 14,15 are not symmetrically arranged on either side of the transverse centreline 16 of the sanitary napkin 1. The position of the fold lines 14,15 are decided by a number of factors, such as the length of the sanitary napkin 1 in relation to the length and positioning of the attachment flaps 22,23 along the side edges 8,9 of the sanitary napkin. The size and positioning of the adhesive regions 24,25 on the attachment flaps 22,23 have also a certain influence on how the packaging is folded together, as well as how the sanitary napkin is placed in the packaging wrapper 17. Thus, the exact position for the fold lines 14,15 can vary somewhat between different sized and different shaped absorbent products and packaging wrappers.

Once folded together the package 30 is sealed by the folded-together side edges 20,21 of the packaging wrapper 17 being welded together by heat or ultrasound. The weld seals 32 are suitably arranged in such a manner that the package 30 can be opened without the packaging wrapper being ripped apart in an uncontrolled manner. This can be achieved, for example, by some of the surfaces in the weld seal 32 being treated with a release agent, or by the seals 32 deforming the material in the packaging wrapper 17 in such a manner that the joint 32 acts as a tear line for opening of the package 30.

In order to hold the packaging hygienically closed, a tape tab 33 is applied on the transverse end 18 of the packaging wrapper 17 which lies on the outside 31 of the packaging 30. Such a sealing can naturally also be made through the open transverse end 18 being welded or glued against the outside 31 of the package 30.

When the package 30 shown in FIG. 3 is to be opened, the same folding movements used during the construction of the package 30 occur in a reversed order. Thus the last folded-in end part 11 of the napkin 1 is folded out together with the packaging wrapper 17. In this way the closure of the edges 20,21 of the package 30 is broken by the packaging material being torn apart along the welded seals 32, or through the seals 32 being opened. The adhesive seal 29 between the end part 28 of the protective layer 26 of the attachment flaps 22,23 fixed on the outside 31 of the packaging wrapper 17, however, is not broken, and the protective layer 26 remains fixed to the packaging wrapper 17. When subsequently the first folded-in end part 12 of the sanitary napkin 1 and the packaging wrapper 17 are folded out, the remaining edge closure 32 of the package 30 is broken and the first part 27 of the protective layer 26 is released at the same time from the adhesive 24,25 on the attachment flaps 22,23.

Figure 4:
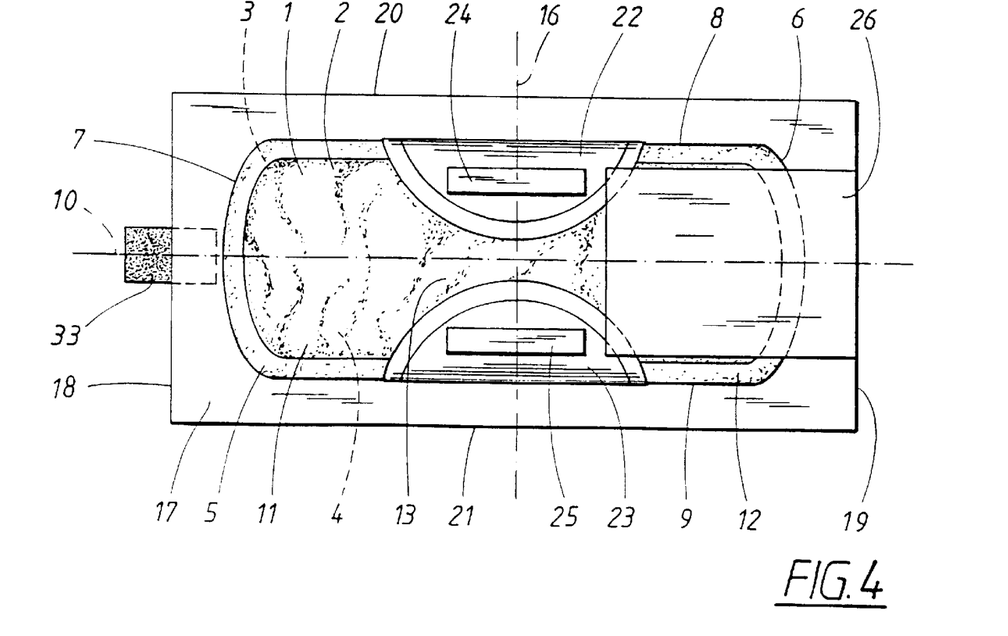
FIG. 4 shows an open packaging with a sanitary napkin.

The completely opened package is shown in FIG. 4. The sanitary napkin 1 is, in the same manner as in FIG. 1, releasably fixed to the packaging wrapper 17 by means of the fastening means attached to the liquid-impermeable covering layer 3. The attachment flaps 22,23 are still folded in over the liquid-permeable covering layer 2 of the sanitary napkin but the adhesive surfaces 24,25 on the attachment flaps 22,23 are exposed. The protective layer 26, which in the package 30 covers the adhesive surfaces 24,25 on the attachment flaps 22,23, is removed from the attachment flaps 22,23 and is instead firmly anchored on the packaging wrapper 17 through the transverse bead of adhesive 29 on the second part 28 of the protective layer 26 being fastened against the outside 31 of the packaging wrapper 17.

Immediately after the opening of the package 30, the protective layer 26, as shown in FIG. 4, remains folded over the liquid-permeable layer 2 of the sanitary napkin at the second end part 12 of the napkin. The protective layer 26 is, however, not attached to any part of the sanitary napkin 1, but can easily be folded away. Subsequently, the napkin can be removed from the packaging wrapper 17 and fastened in the crotch part of a pair of underpants. The packaging wrapper 17 can either be thrown away at the same time as the protective layer 26 of the attachment flaps 22,23, or can be used for wrapping a used sanitary napkin which is to be thrown away.

Figure 5:
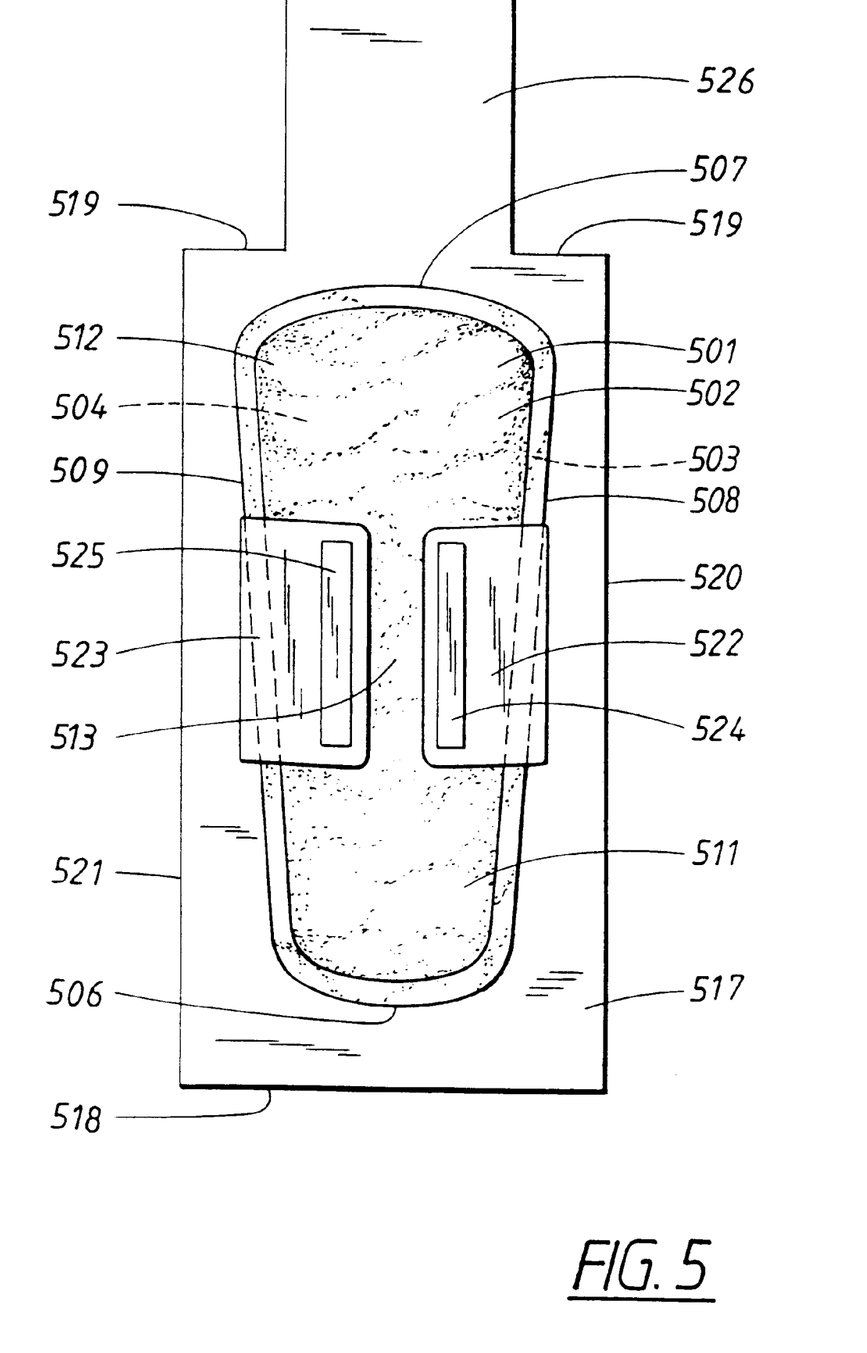
FIG. 5 shows a sanitary napkin placed upon a packaging wrapper, according to a second embodiment of the invention.

FIG. 5 shows a sanitary napkin 501 arranged on a packaging wrapper 517 according to another embodiment of the invention. The sanitary napkin 501 has essentially the same construction as the sanitary napkin shown in FIG. 1, and has therefore a liquid-permeable covering layer 502, a liquid-impermeable covering layer 503, and an absorption body 504 enclosed between the covering layers 502,503. The sanitary napkin has a trapezoidal shape and has a narrow rear part 511, intended during use to be facing backwards towards the seat of the user, a wider front part 512 intended during use to be facing forwards towards the stomach of the user, and a centre part 513 arranged between the rear part 511 and the front part 512. The sanitary napkin 501 further has a transverse rear edge 506, a transverse front edge 507, and two oblique side edges 508,509 extending between the rear edge 506 and the front edge 507.

A fastening means (not shown in the Figure) is arranged on the liquid-impermeable covering layer 503 of the sanitary napkin 501, in the form of a surface covered with small hooklike projections, a so-called hook surface. Such a fastening means fastens in a removable manner against textile material by gripping on fibres on the surface of the material.

The sanitary napkin is further equipped with attachment flaps 522,523 projecting out from the longitudinal side edges 508, 509, with the shape of rounded rectangles. Each attachment flap 522,523 has a surface of self-adhesive pressure-sensitive glue 524,525 for attaching the flaps 522,523 on the outside of the crotch region in a pair of underpants. During packaging of the sanitary napkin, the attachment flaps 522, 523 are folded-in against the liquid-permeable covering layer 502 of the sanitary napkin.

The sanitary napkin is placed on a packaging wrapper 517 made of paper, plastic or similar. The packaging wrapper 517 has essentially a rectangular shape with a rear transverse edge 518, a front transverse edge 519 and two longitudinal side edges 520,521. At the front transverse edge 519 the packaging wrapper 517 is equipped with a protective layer in the form of a projecting protective flap 526. The protective flap 526 also has a rectangular shape and is treated with a release agent on the surface in the Figure facing away from the sanitary napkin.

In order to form a package, the sanitary napkin is folded up together with the packaging wrapper 517 in a similar manner to that described in connection with FIGS. 1–4. However, the protective flap 526 is folded first in over the front edge 507 of the sanitary napkin and thereafter the front part 512 of the sanitary napkin and the part of the packaging wrapper 517 lying in contact with the front part 512 are folded in over the centre part 513 of the sanitary napkin in the direction towards the liquid-permeable covering layer 502. Next, the rear part 511 of the sanitary napkin and the part of the packaging wrapper 517 lying in contact with it, are folded in over the already folded in front part 512. The finished folded package is sealed in the same manner as the package 30 in FIGS. 1–4. Alternatively, the package can be sealed through adhesive being applied along the edges of the packaging wrapper 517 on the surface facing towards the sanitary napkin before the package is folded together. In order to provide openability of such adhesive seals, the edge parts of the packaging wrapper can be treated with release agent. It is also possible to arrange perforations as a tear line inwardly of the adhesive seals. Naturally, it is not necessary for the protective flap 526 to be produced in one piece with the packaging wrapper 517. The protective flap 526 can equally well be a separate piece of material which is fastened on one of the end edges of the packaging wrapper. Such an arrangement has the advantage of reducing the material wasted during manufacturing of the packages, as the protective flaps and the packaging wrappers can be cut from different webs of material. Another advantage is that it is possible to choose different materials for the protective flaps and the packaging wrappers.

Figure 6:
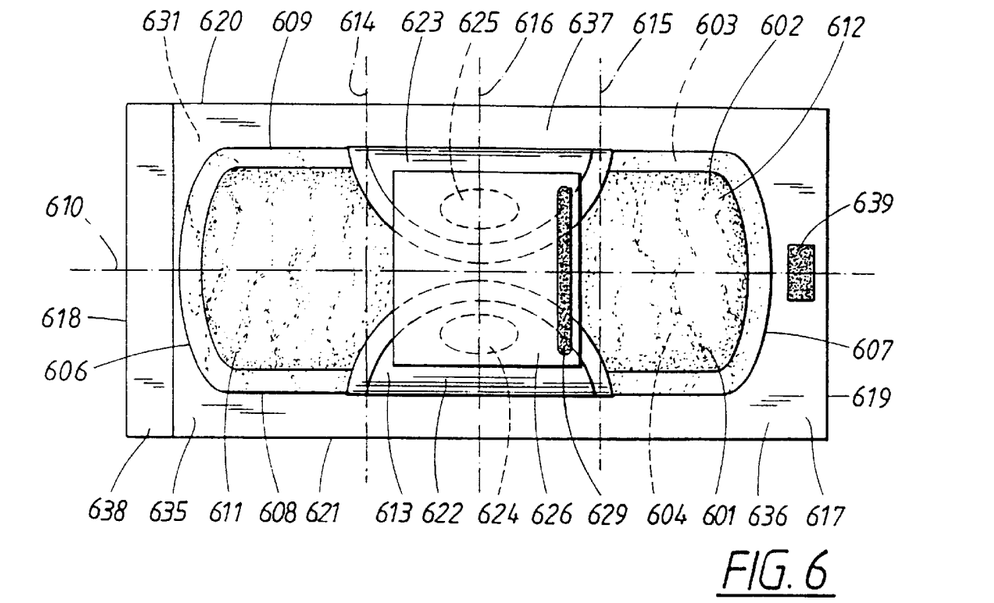
FIG. 6 shows a sanitary napkin placed on a packaging wrapper according to a third embodiment of the invention.

The sanitary napkin 601 shown in FIG. 6 has also principally the same construction as the earlier described sanitary napkins 1,501 and has consequently a liquid-permeable covering layer 602, a liquid-impermeable covering layer 603, and an absorption body 604 enclosed between the covering layers 602,603. The sanitary napkin 601 has an elongated, essentially rectangular shape, and has two end parts 611,612 and a centre part 613 arranged between them. The sanitary napkin 601 further has two longitudinal side edges 608,609 and two rounded, transverse end edges 606, 607.

The sanitary napkin 601 is further equipped with halfmoon-shaped attachment flaps 622,623, projecting from the longitudinal side edges 608,609. Each attachment flap 622,623 has an oval surface of self-adhesive pressure-sensitive glue 624,625 for attaching the flaps 622,623 on the outside of the crotch region in a pair of underpants. The attachment flaps 622,623 are folded in against the liquid-permeable covering layer 602 of the sanitary napkin as a first step in the packaging folding of the sanitary napkin 601.

A rectangular protective flap 626 is further arranged over the adhesive surfaces 624,625 on the attachment flaps 622, 623. The protective flap 626 is covered with a release agent on the surface which lies in contact with the adhesive surfaces 624, 625 so as to be easily removed. A bead of self-adhesive glue 629 is arranged along a transverse edge 634 on the protective flap 626.

The sanitary napkin 601 is equipped with a fastening means (not shown in the Figure), in the form of one or more self-adhesive adhesive surfaces arranged on the liquid-impermeable covering layer 603. The sanitary napkin 601 furthermore lies with the liquid-impermeable covering layer 603 facing towards a rectangular packaging wrapper 617 of flexible material. The packaging wrapper 617 extends out around the edges 606–609 of the sanitary napkin 601 and is treated with a release agent coating over the regions which are in contact with the fastening means on the underside of the sanitary napkin 601. In a similar manner to the sanitary napkin 601, the packaging wrapper 617 has two longitudinal side edges 620,621, two transverse end edges 618,619, a first and a second end part 635,636, and an intermediate centre part 637. A release-agent-free area 638 is arranged along a first transverse edge 618 on the inside of the packaging wrapper, i.e. on the surface of the packaging wrapper 617 facing towards the liquid-permeable covering layer 602 of the sanitary napkin 601. The release agent-free area 638 extends out past the corresponding transverse end edge 606 of the sanitary napkin 601 and is arranged at the first end part 635 of the packaging wrapper 617, which is the end part which in FIG. 6 is arranged furthest away from the transverse bead of adhesive 629 on the protective layer 626 of the attachment flaps 622, 623. The release agent-free area is arranged either through an area of the interior of the packaging wrapper 617 being left free from the release agent treatment, or through a part of the packaging wrapper 617 being folded in towards the first end part 635. In the latter arrangement the release agent-free area 638 is formed from the release agent-free outside of the packaging wrapper 617.

On the opposing second end part 636 of the packaging wrapper 617, between the second transverse end edge 607 of the sanitary napkin 601 and the second transverse end edge 619 of the packaging wrapper 617, a region of self-adhesive glue 639 is arranged, also on the release agent-treated interior of the packaging wrapper 617.

The folding together of the sanitary napkin 601 and the packaging wrapper 617 to a package takes place along a first and a second transverse fold line 614,615, arranged essentially symmetrically on either side of transverse centreline 616 of the sanitary napkin. The first end part 635 of the packaging wrapper 617 is, together with the corresponding end part 611 of the sanitary napkin 601, first folded in over the centre part 613 of the sanitary napkin along the first fold line 614. The folding takes place in a direction towards the liquid-permeable covering layer 602 of the sanitary napkin. The region 638 on the packaging wrapper 617 which is free from release agent, fastens in this manner against the bead of adhesive 629 on the protective layer 626 on the attachment flaps 622,623. The adhesive strength of the bead of adhesive 629 is so high that the seal between the protective layer 626 and the packaging wrapper 617 is considerably stronger than the removable joint between the protective layer 626 and the adhesive surfaces 624,625 on the attachment flaps 622,623.

Next, the second end part 636 of the packaging wrapper 617, together with the corresponding end part 612 of the sanitary napkin 601 are folded in over the centre part 613 of the sanitary napkin. This folding also takes place in a direction towards the liquid-permeable covering layer 602. In this way the adhesive surface 639 fastens against the second end part 636 of the packaging wrapper 617 against the outside 631 of the first end part 635 of the packaging wrapper 617. In this manner the transverse edge 619 on the outside of the package formed in this way will be hygienically closed until the package is opened. When the sanitary napkin is to be used, the folded-together package is readily opened, without tearing of the packaging material, by the adhesive surface 639 being released from the release agent-treated inside of the packaging wrapper 617 and thereby is transferred to the outside 631 of the packaging wrapper. In a similar manner to the earlier described embodiments, the folded-together longitudinal side edges 620,621 are sealed, for example through gluing or welding with heat or ultrasound.

The package is opened through the adhesive sealing 639 on the outside transverse edge 619 of the packaging wrapper 617 being broken, after which the side edge seals are opened through the packaging wrapper being folded out together with the sanitary napkin. A package opened in this manner will appear essentially as shown in FIG. 6. The protective layer 626 over the adhesive surfaces 624, 625 on the attachment flaps 622,623 is removed, however, when the packaging is opened, through the transverse bead of adhesive 629 on the protective layer 626 being firmly attached to the packaging wrapper 617 and following with this when it is folded away in the direction from the liquid-permeable covering layer 602 on the centre part 613 of the sanitary napkin. The sanitary napkin can then subsequently be removed from the packaging wrapper 617 which can be thrown away or can be reused as a wrapper for a used sanitary napkin which is to be thrown away.

Figure 7:
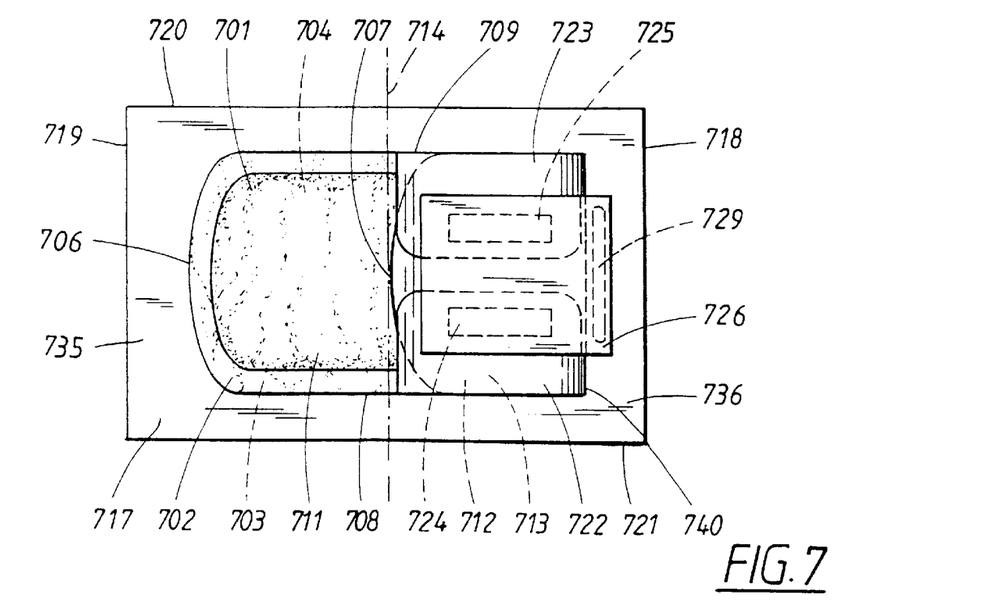
FIG. 7 shows a sanitary napkin placed upon a packaging wrapper according to a fourth embodiment of the invention.

FIG. 7 shows a sanitary napkin of the same principal construction as the earlier described sanitary napkins. Accordingly, the sanitary napkin 701 has an absorption body 704 contained between a liquid-permeable covering layer 702 and a liquid-impermeable covering layer 703. The sanitary napkin 701 is essentially rectangular with two longitudinal side edges 708, 709, two transverse end edges 706,707, a first end part 711, a second end part 712, and a centre part 713 arranged between the end parts 711,712. A rounded rectangular attachment flap 722,723 is arranged on each of the side edges 708,709. The attachment flaps 722, 723 are formed from parts 705 of the covering layers 702,703 extending out beyond the edges of the absorption body 704 and are equipped with self-adhesive adhesive surfaces 724,725 on the liquid-impermeable covering layer 703.

The sanitary napkin 701 is shown partially folded in FIG. 7, with the first end part 711 folded over the centre part 713 in a direction towards the liquid-permeable covering layer 702. The attachment flaps 722,723 are subsequently folded in over the centre part 713 of the sanitary napkin, outside the folded-in end part 711. The sanitary napkin 701 folded in this manner is placed on a packaging wrapper 717 which is shorter than the unfolded sanitary napkin 701, but longer than the partially folded sanitary napkin such as shown in FIG. 7. The packaging wrapper 717 is rectangular and extends out beyond the folded sanitary napkin 701 around the whole of its periphery. The packaging wrapper 717 has two longitudinal side edges 720,721 and two transverse end edges 718,719. A rectangular protective flap 726 is attached on the packaging wrapper 717 between the folded edge 740 on the sanitary napkin 701 and the corresponding first transverse edge 718 of the packaging wrapper 717. The protective flap 726 extends in the direction away from the first transverse edge 718 of the packaging wrapper 717, in over the sanitary napkin 701, and is in contact with the adhesive surfaces 724,725 on the attachment flaps 722,723. The surface of the protective flap 726 which is in contact with the adhesive surfaces 724,725 is release agent-treated.

The packaging is closed through the second end part 712 of the sanitary napkin 701 being folded in over the protective flap 726, together with the packaging wrapper 717. The folding occurs along a transverse fold line 714 which divides the packaging wrapper 717 in two essentially equally large parts 735,736. The edge parts 718–721 of the packaging wrapper 717 are sealed in a conventional manner through gluing or welding. The packaging is opened through the edge sealings being ripped open. Next, the protective flap 726 is folded away from the attachment flaps 722,723 and the sanitary napkin 701 is released from the packaging wrapper.

The arrangement shown in FIG. 7 requires that the fastening means of the sanitary napkin 701 does not adhere to the material 702 on the inside of the attachment flaps 722,723, or that the first folded-in end part 711 of the sanitary napkin is completely without fastening means. This embodiment is therefore less preferred. It is also a disadvantage that the protective flap 626 is not automatically released from the adhesive surfaces 624,625 on the attachment flaps 622,623 when the packaging is opened.

The invention should not be considered to be limited to the embodiments described here. For example, it is obvious that the shape of the protective flaps, the absorbent products or the packaging wrappers has no special relevance for the invention but can take any form whatsoever which it technically suitable or which is found to be aesthetically attractive. It is, however, advantageous if the the width of the protective flap is less than the width of packaging wrapper, whereby the number of layers of material in the edge joints of the packaging can be minimized.

In the same way the invention is not limited to use for sanitary napkins of a particular shape or construction, but all absorbent products which have attachment flaps provided with adhesive arranged on their side edges can be packaged in accordance with the invention.

Furthermore, all conceivable combinations of the described embodiments are intended to be included within the framework of the invention.

For example, instead of a single protective flap which covers the adhesive on both the attachment flaps, it is possible to arrange separate protective flaps for the attachment flaps. It is, however, a less preferred embodiment as it complicates the manufacturing of the packaging according to the invention.

What is claimed is:

1. An absorbent product comprising:
   an essentially elongated body having two transverse end edges, two longitudinal side edges, two end regions and a center region arranged between the two end regions, a liquid-permeable surface, a liquid-impermeable surface and, an absorption body arranged between the liquid-permeable and liquid-impermeable surfaces;
   at least one attachment flap arranged along one of the longitudinal side edges of the body and folded over the liquid-permeable surface of the body;
   at least one adhesive fastener on a surface of the at least one attachment flap facing away from the body in the folded position;
   a packaging wrapper of an essentially elongated shape having two longitudinal side edges, two transverse end edges, an inside surface, and an outside surface wherein the inside surface of the packaging wrapper lies on the liquid-impermeable surface of the body and is folded along at least one transverse fold line through the body to form a package;
   at least one protective layer with a release agent-treated surface for removably covering the at least one adhesive fastener of the at least one attachment flap, the protective layer comprising a piece of material that is separate from the package wrapper and the protective layer having a part which is firmly connected to the outside surface of the packaging wrapper near one of the transverse end edges of the packaging wrapper, wherein the connection between the protective layer and the packaging wrapper is stronger than the adhesion between the protective layer and the at least one adhesive fastener on the at least one attachment flap so that the protective layer remains connected to the packaging wrapper even after the package is opened.

2. The absorbent product according to claim 1, wherein the body has two attachment flaps, each of the attachment flaps having an adhesive fastener, wherein the adhesive fastener comprises a self-adhesive glue, and is arranged on each of the longitudinal side edges of the product, and the at least one protective layer covers the self-adhesive glue on both of the attachment flaps.

3. The absorbent product according to claim 1, wherein the body further comprises an adhesive on at least one adhesive region on the liquid-impermeable surface of the body and the packaging wrapper removably covers the adhesive.

4. The absorbent product according to claim 1, wherein the protective layer extends over one of the transverse end edges of the body and is arranged between the two end regions and covers a portion of the center region of the body.

5. The absorbent product according to claim 1, wherein the body is folded together with the packaging wrapper along a second transverse fold line.

6. The absorbent product according to claim 5, wherein the at least one and second transverse fold lines divide the body into three parts, essentially corresponding with the end regions and the center region of the body.

7. The absorbent product according to claim 1, wherein a width in the transverse direction of the protective layer is less than a width of the packaging wrapper in the transverse direction.

8. The absorbent product according to claim 1, wherein the absorbent product is a sanitary napkin.

9. The absorbent product of claim 1, wherein the absorbent product is a pantyliner.

10. The absorbent product of claim 1, wherein the absorbent product is an incontinence protector.

11. A package for holding a folded absorbent product equipped with projecting attachment flaps, which package comprises:
    a packaging wrapper of such shape and extension that it can enclose the folded absorbent product, the packaging wrapper having an inside surface and an outside surface;
    a protective layer removably attachable to an adhesive arranged on the projecting attachment flaps of the folded product wherein the protective layer is formed of a separate piece of material and has means for firm attachment of the protective layer to the outside surface of the packaging wrapper.

12. The package of claim 11, wherein the inside surface of the packaging wrapper is treated with a release agent.

13. The package of claim 11, wherein the packaging wrapper has a first end and a second end and the inside surface of the first end overlaps the outside surface of the second end.

* * * * *